US 6,852,904 B2

(12) United States Patent  (10) Patent No.: US 6,852,904 B2
Sun et al.  (45) Date of Patent: Feb. 8, 2005

(54) CELLULOSE FIBERS TREATED WITH ACIDIC ODOR CONTROL AGENTS (75) Inventors: Tong Sun, Nennah, WI (US); Chien-Ping Hsu, Appleton, WI (US); Kelly M. Sedlachek, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 148 days.

(21) Appl. No.: 10/025,836

(22) Filed: Dec. 18, 2001

(65) Prior Publication Data

US 2003/0144637 A1 Jul. 31, 2003

(51) Int. Cl.$^7$ .......................... A61F 13/15; A61F 13/20
(52) U.S. Cl. ........................................ 604/359; 604/360
(58) Field of Search ............................... 604/359–360, 604/367, 374–375

(56) References Cited

U.S. PATENT DOCUMENTS

| 2,799,241 A | | 7/1957 | Wurster .................... 118/24 |
| 3,089,824 A | | 5/1963 | Wurster .................... 167/82 |
| 3,117,024 A | | 1/1964 | Ross ....................... 118/49 |
| 3,196,827 A | | 7/1965 | Wurster et al. ............. 118/24 |
| 3,207,824 A | | 9/1965 | Wurster et al. ............ 264/117 |
| 3,224,926 A | * | 12/1965 | Bernardin ................. 162/146 |
| 3,241,520 A | | 3/1966 | Wurster et al. ............. 118/62 |
| 3,253,944 A | | 5/1966 | Wurster .................... 117/100 |
| 3,338,992 A | | 8/1967 | Kinney ..................... 264/24 |
| 3,341,394 A | | 9/1967 | Kinney ..................... 161/72 |
| 3,485,706 A | | 12/1969 | Evans ...................... 161/72 |
| 3,502,538 A | | 3/1970 | Petersen ................... 161/150 |
| 3,502,763 A | | 3/1970 | Hartmann .................. 264/210 |
| 3,533,725 A | * | 10/1970 | Bridgeford ................. 8/115.6 |
| 3,534,075 A | | 10/1970 | Andress, Jr. ............. 260/404.5 |
| 3,542,615 A | | 11/1970 | Dobo et al. ................ 156/181 |
| 3,658,790 A | * | 4/1972 | Bernardin ................... 536/34 |
| 3,691,154 A | * | 9/1972 | Bernardin .................. 8/116.1 |
| 3,692,618 A | | 9/1972 | Dorscher et al. ............ 161/72 |
| 3,707,148 A | | 12/1972 | Bryce ..................... 128/284 |
| 3,794,034 A | | 2/1974 | Jones, Sr. ................ 128/290 |
| 3,802,817 A | | 4/1974 | Matsuki et al. ............. 425/66 |
| 3,849,241 A | | 11/1974 | Butin et al. ............... 161/169 |
| 3,854,868 A | * | 12/1974 | Ward et al. ................ 8/116.1 |
| 3,855,046 A | | 12/1974 | Hansen et al. ............. 161/150 |
| 3,879,376 A | | 4/1975 | Vanlerberghe et al. ... 260/211 R |
| 3,901,236 A | | 8/1975 | Assarsson et al. ......... 128/284 |
| 3,903,259 A | | 9/1975 | Hart ....................... 424/76 |
| 3,920,020 A | | 11/1975 | Kraskin .................... 128/290 |
| 3,953,608 A | | 4/1976 | Vanlerberghe et al. ...... 424/361 |
| 4,076,663 A | | 2/1978 | Masuda et al. .......... 260/17.4 GC |
| 4,100,324 A | | 7/1978 | Anderson et al. ........... 428/288 |

(List continued on next page.)

FOREIGN PATENT DOCUMENTS

| AU | 36037 A | 2/2000 | .......... A61L/15/46 |
| DE | 19857547 | 8/2000 | ............ C08L/5/08 |
| DE | 19857548 | 8/2000 | ............ C08L/5/08 |

(List continued on next page.)

OTHER PUBLICATIONS

Dharmawardana, Udeni R. et al.: *A Surface Tension Method for Determining Binding Constants For Cyclodextrin Inclusion Complexes of Ionic Surfactants* (May 1993) (pp. 2258–2263), Institute for Applied Surfactant Research, The University of Oklahoma.

Primary Examiner—Larry I. Schwartz
Assistant Examiner—Michele Kidwell
(74) Attorney, Agent, or Firm—Pauley Petersen & Erickson (57) ABSTRACT

An odor control system is formed by treating cellulose fibers with a partially neutralized carboxylic acid odor control agent. The odor control system absorbs odor and inhibits formation of various odor-producing bacteria. The odor control system is useful in the absorbent cores of a wide variety of personal care and medical absorbent garments.

29 Claims, 1 Drawing Sheet

U.S. PATENT DOCUMENTS

| | | | |
|---|---|---|---|
| 4,200,735 A * | 4/1980 | Sano et al. | 536/30 |
| 4,273,786 A | 6/1981 | Kraskin | 424/319 |
| 4,286,082 A | 8/1981 | Tsubakimoto et al. | 526/240 |
| 4,300,561 A | 11/1981 | Kaczmarzyk et al. | 128/285 |
| 4,340,563 A | 7/1982 | Appel et al. | 264/518 |
| 4,356,190 A | 10/1982 | Kraskin | 424/319 |
| 4,377,167 A | 3/1983 | Kaczmarzyk et al. | 128/285 |
| 4,385,632 A | 5/1983 | Odelhög | 604/360 |
| 4,479,795 A | 10/1984 | Mustacich et al. | 604/53 |
| 4,574,150 A | 3/1986 | Austin | 536/20 |
| 4,610,678 A * | 9/1986 | Weisman et al. | 604/368 |
| 4,617,230 A | 10/1986 | Shah et al. | 428/288 |
| 4,623,588 A | 11/1986 | Nuwayser et al. | 428/402.24 |
| 4,638,058 A | 1/1987 | Brandt et al. | 536/103 |
| 4,675,140 A | 6/1987 | Sparks et al. | 264/4.3 |
| 4,818,464 A | 4/1989 | Lau | 264/510 |
| 5,061,792 A | 10/1991 | Albisetti et al. | 536/20 |
| 5,108,820 A | 4/1992 | Kaneko et al. | 428/198 |
| 5,137,537 A * | 8/1992 | Herron et al. | 8/120 |
| 5,161,686 A | 11/1992 | Weber et al. | 206/440 |
| 5,206,341 A | 4/1993 | Ibay et al. | 528/361 |
| 5,254,168 A | 10/1993 | Littman et al. | 118/666 |
| 5,310,865 A | 5/1994 | Enomoto et al. | 528/361 |
| 5,336,552 A | 8/1994 | Strack et al. | 428/224 |
| 5,348,667 A | 9/1994 | Bacon et al. | 252/8.6 |
| 5,382,400 A | 1/1995 | Pike et al. | 264/168 |
| 5,429,628 A | 7/1995 | Trinh et al. | 604/359 |
| 5,533,990 A | 7/1996 | Yeo | 604/363 |
| 5,534,165 A | 7/1996 | Pilosof et al. | 252/8.91 |
| 5,554,597 A | 9/1996 | Yu et al. | 514/557 |
| 5,561,158 A | 10/1996 | Yu et al. | 514/557 |
| 5,571,782 A | 11/1996 | Trinh et al. | 512/4 |
| 5,578,563 A | 11/1996 | Trinh et al. | 510/513 |
| 5,591,146 A | 1/1997 | Hasse | 604/359 |
| 5,593,670 A | 1/1997 | Trinh et al. | 424/76.1 |
| 5,625,015 A | 4/1997 | Brinen et al. | 526/160 |
| 5,635,191 A | 6/1997 | Roe et al. | 424/402 |
| 5,648,067 A | 7/1997 | Dillenburg et al. | 424/65 |
| 5,663,134 A | 9/1997 | Trinh et al. | 510/406 |
| 5,668,097 A | 9/1997 | Trinh et al. | 510/293 |
| 5,670,475 A | 9/1997 | Trinh et al. | 510/470 |
| 5,690,919 A | 11/1997 | Rockl et al. | 424/65 |
| 5,698,476 A | 12/1997 | Johnson et al. | 442/121 |
| 5,714,137 A | 2/1998 | Trinh et al. | 424/76.4 |
| 5,714,445 A | 2/1998 | Trinh et al. | 510/103 |
| 5,718,887 A | 2/1998 | Wolf et al. | 424/65 |
| 5,733,272 A | 3/1998 | Brunner et al. | 604/359 |
| 5,753,211 A | 5/1998 | Garson et al. | 424/61 |
| H1732 H | 6/1998 | Johnson | 428/68 |
| 5,769,833 A | 6/1998 | Hasse | 604/359 |
| 5,770,711 A | 6/1998 | Greene et al. | 536/18.6 |
| 5,780,020 A | 7/1998 | Peterson et al. | 424/65 |
| 5,785,697 A | 7/1998 | Trombetta et al. | 604/378 |
| 5,821,215 A | 10/1998 | Crudden et al. | 510/392 |
| 5,865,792 A | 2/1999 | Ledger et al. | 604/20 |
| 5,871,718 A | 2/1999 | Lucas et al. | 424/65 |
| 5,871,719 A | 2/1999 | Lucas et al. | 424/65 |
| 5,874,070 A * | 2/1999 | Trinh et al. | 424/65 |
| 5,874,164 A | 2/1999 | Caldwell | 428/306.6 |
| 5,928,631 A | 7/1999 | Lucas et al. | 424/65 |
| 5,932,495 A | 8/1999 | Boney et al. | 442/121 |
| 5,942,217 A | 8/1999 | Woo et al. | 424/76.1 |
| 5,955,093 A | 9/1999 | Woo et al. | 424/401 |
| 5,961,996 A | 10/1999 | Garson et al. | 424/401 |
| 5,968,404 A | 10/1999 | Trinh et al. | 252/8.91 |
| 5,997,759 A | 12/1999 | Trinh et al. | 252/8.91 |
| 5,998,511 A | 12/1999 | Westland et al. | 524/13 |
| 6,001,343 A | 12/1999 | Trinh et al. | 424/76.4 |
| 6,031,147 A | 2/2000 | Gross | 604/359 |
| 6,033,486 A | 3/2000 | Andros | 134/6 |
| 6,033,679 A | 3/2000 | Woo et al. | 424/401 |
| 6,066,673 A | 5/2000 | McIver et al. | 514/634 |
| 6,100,233 A | 8/2000 | Sivik et al. | 512/26 |
| 6,106,738 A | 8/2000 | Woo et al. | 252/8.91 |
| 6,114,496 A | 9/2000 | Otera et al. | 528/361 |
| 6,156,296 A | 12/2000 | Riedel et al. | 424/70.1 |
| 6,190,694 B1 | 2/2001 | Mizushima et al. | 424/451 |
| 6,229,062 B1 | 5/2001 | Mandell et al. | 604/367 |

FOREIGN PATENT DOCUMENTS

| | | | |
|---|---|---|---|
| EP | 311 344 | 4/1989 | A61L/15/00 |
| EP | 392 528 | 10/1990 | A61L/15/46 |
| EP | 392 607 | 10/1990 | C11D/17/04 |
| EP | 392 608 | 10/1990 | C08B/37/16 |
| EP | 510 619 | 10/1992 | A61F/13/15 |
| EP | 562 620 | 9/1993 | A61L/15/46 |
| EP | 685 213 | 12/1995 | A61F/13/15 |
| EP | 811 390 | 12/1997 | A61L/15/46 |
| EP | 811 391 | 12/1997 | A61L/15/46 |
| EP | 813 848 | 12/1997 | A61F/13/15 |
| EP | 953 589 | 11/1999 | C08G/63/80 |
| JP | 01-005553 | 1/1989 | A61L/09/01 |
| JP | 1-104885 | 4/1989 | D06M/15/564 |
| JP | 02-190187 | 7/1990 | C12N/11/14 |
| JP | 03-109351 | 5/1991 | C07C/69/675 |
| JP | 2771863 | 7/1998 | C07C/69/675 |
| JP | 3042691 B2 | 5/2000 | C12N/11/14 |
| WO | 22500 | 10/1994 | A61L/15/46 |
| WO | 17175 | 6/1995 | A61K/9/70 |
| WO | 04937 | 2/1996 | A61L/9/01 |
| WO | 05358 | 2/1996 | D06M/15/11 |
| WO | 24318 | 8/1996 | A61F/13/15 |
| WO | 07455 | 2/1998 | A61L/9/01 |
| WO | 17239 | 4/1998 | A61K/7/32 |
| WO | 17240 | 4/1998 | A61K/7/32 |
| WO | 18439 | 5/1998 | A61K/7/32 |
| WO | 26808 | 6/1998 | A61L/9/01 |
| WO | 99/61518 | 2/1999 | C08J/9/00 |
| WO | 99/32697 | 7/1999 | D06M/15/03 |
| WO | 45973 | 9/1999 | A61L/15/44 |
| WO | 45974 | 9/1999 | A61L/15/44 |
| WO | 55814 | 11/1999 | C11D/3/22 |
| WO | 10500 | 3/2000 | A61F/13/15 |
| WO | 00/50098 | 8/2000 | A61L/15/48 |
| WO | 62826 | 10/2000 | A61L/15/18 |
| WO | 01/32226 | 5/2001 | A61L/15/20 |

* cited by examiner

FIG. 1

CELLULOSE FIBERS TREATED WITH ACIDIC ODOR CONTROL AGENTS

FIELD OF THE INVENTION

This invention relates to an odor control system including cellulose fibers treated with an acidic odor control agent, and to a method of incorporating acidic odor control agents into cellulose fibers. The treated cellulose fibers are useful in the absorbent cores of personal care absorbent articles, medical absorbent articles, and the like.

BACKGROUND OF THE INVENTION

For many personal care absorbent articles, medical absorbent articles, and the like, it is desirable to reduce, prevent, or eliminate odors during use. For diapers and other incontinence products, it is desirable to reduce or eliminate the odor of ammonia which is present in urine. For feminine hygiene products, it is desirable to reduce or eliminate the odors of trimethylamine and triethylamine. Other common odor-producing substances include isovaleric acid, dimethyl disulfide, and dimethyl trisulfide.

Odor control agents include odor inhibitors, odor absorbers, odor adsorbers and other compounds which suppress odors. Odor inhibitors prevent the odor from forming. For example, U.S. Pat. No. 4,273,786 to Kraskin teaches the use of an aminopolycarboxylic acid compound for inhibiting the formation of ammonia from urea in urine. Odor absorbers and adsorbers remove odor after it is formed. Examples of odor control agents that remove odor by absorption or adsorption include activated carbon, silica, and cyclodextrin.

Acidic odor control agents based on carboxylic acids and their derivatives are used to neutralize or inhibit formation of odors from ammonia and other basic odor-forming compounds. Ammonia, released from aqueous ammonium hydroxide, is one of the primary odor-producing substances in urine. One of the drawbacks of acidic odor control agents is they are not inherently durable, i.e., they pass into solution after one or more insults with aqueous liquid, and may acidify the liquid. If some of the acidified aqueous liquid leaks from the absorbent article and passes to the wearer's skin, the wearer may experience itching, rash, and/or other uncomfortable effects.

Previously, acidic odor control agents have been applied to absorbent articles in the form of powders, coatings, and the like, which can be easily dissolved. There is a need or desire for absorbent articles having durable acidic odor control agents, which retain their odor control functions and do not pass into solution after one or more insults with aqueous liquid.

DEFINITIONS

The term "cellulose fibers" refers to fibers from wood, paper, woody plants, and certain non-woody plants. Woody plants include, for example, deciduous and coniferous trees. Non-woody plants include, for instance, cotton, flax, esparto grass, milkweed, straw, jute hemp, and bagasse.

The term "average cellulose fiber length" refers to a weighted average length of cellulose fibers determined using a Kajaani fiber analyzer Model No. FS-100 available from Kajaani Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The weighted average fiber lengths may be expressed by the following equation:

$$\sum_{x_1>0}^{k} (X_i * n_1)/n$$

where
k=maximum fiber length,
$X_i$=individual fiber length,
$n_i$=number of fibers having length $X_i$ and
n=total number of fibers measured.

The term "fiber consistency" refers to a weight ratio of dry fiber/(dry fiber plus water) in an aqueous mixture.

The term "carboxylic acid-based odor control agent" includes odor control agents based on carboxylic acids and/or their partially neutralized salts. The term "multi-carboxylic acid-based odor control agent" includes odor control agents based on dicarboxylic acids, tricarboxylic acids, polycarboxylic acids, etc., having two or more carboxylic acid groups, and/or their partially neutralized salts.

The term "hydroxyl multi-carboxylic acid" (HMCA) refers to a compound containing at least one hydroxyl (—OH) group and at least two carboxyl (—COOH) groups, including citric acid, malic acid, tartaric acid, and the like.

The term "polycarboxylic acid" (PCA) refers to a polymer or copolymer that contains carboxyl (—COOH) groups on its repeating units, including polyacrylic acid, acrylic acid copolymers, polymaleic acid, maleic acid copolymers, and the like.

The term "degree of neutralization" (DON) refers to a ratio of a molar equivalent number of (—COOM groups)/(a sum of —COOM groups and —COOH groups) in a partially neutralized HMCA or PCA containing system, where the —COOM groups represent a salt formed using a transition metal (M) such as Zn, Cd, Zr, Cr, Ti, Cu or the like.

The term "odor control system" refers collectively to individual odor control agents, and combinations (by chemical reaction and/or blending) of two or more odor control agents.

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "personal care absorbent product" includes without limitation diapers, training pants, swim wear, absorbent underpants, baby wipes, adult incontinence products, and feminine hygiene products.

The term "medical absorbent product" includes without limitation garments, underpads, bandages, absorbent drapes, and medical wipes.

"Superabsorbent" or "superabsorbent material" refers to a water-swellable, water-insoluble organic or inorganic material capable, under the most favorable conditions, of absorbing at least about 15 times its weight and, more desirably, at least about 20 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

SUMMARY OF THE INVENTION

The present invention is directed to an odor control system which includes cellulose fibers treated with salts of a transition metal derived from partially neutralized hydroxyl multi-carboxylic acid (HMCA) and/or polycarboxylic acid (PCA). Due to the bacteriostatic activity, chelating capability and acidity of the partially neutralized salts of the HMCA and PCA, the system can serve as an inhibitor to prevent or reduce the generation of ammonia and other basic odor-forming compounds, and also as an odor absorber of the generated ammonia and other basic odor-forming compounds (via neutralization and chelating reaction).

The odor control system is prepared as follows. First, weigh out calculated amount of untreated cellulose fiber, water, a HMCA and/or PCA, and a transition metal containing compound (e.g., the oxide, hydroxide and/or carbonate of a transition metal). The ingredients are then thoroughly blended at ambient temperature. The resulting blend is heated using a temperature and time sufficient to remove the water. The resulting heated dry cellulose fibers are then fiberized (separated) using a fiberizer. The separated treated cellulose fibers may optionally be further cured at an elevated temperature.

The treated cellulose fibers exhibit varying levels of odor absorption and odor inhibition capability depending on the specific carboxylic acid odor control agent used and its add-on level to the fiber. The treated cellulose fibers can be employed in the absorbent core of a personal care absorbent article, a medical absorbent article, and the like. The treated cellulose fibers may be combined with other fibers (e.g., untreated cellulose fibers, synthetic fibers, and etc.), with superabsorbent materials, and with other ingredients to make an absorbent core.

DETAILED DESCRIPTION OF THE PRESENTLY PREFERRED EMBODIMENTS

The present invention is directed to an odor control system which includes cellulose fibers treated with salts of a transition metal derived from partially neutralized HMCA and/or PCA. Cellulose has the general chemical formula $(C_6H_{10}O_5)_n$, configured as follows:

Cellulose

While not wishing to be bound by theory, it is possible that cellulose reacts or otherwise bonds with partially neutralized HCMA and/or PCA (e.g., RCOOM) in the presence of heat, for a time sufficient to cause dehydration, to yield an ester:

Cellulose Modified with Odor Control Agent

The resulting odor control system is believed to be relatively stable, and is not easily degraded by a mere infusion of aqueous liquid. For this reason, the odor control system based on modified cellulose has odor control properties which are relatively durable, and withstand insults with aqueous liquids.

The cellulose fibers may have high average fiber lengths, low average fiber lengths, or a combination of high and low average fiber length fibers. High average fiber length fibers generally have an average fiber length greater than about 1.5 mm, suitably about 1.5–6 mm, when measured using an optical fiber analyzer such as the Kajaani tester described above. Low average fiber length fibers generally have an average fiber length less than about 1.5 mm, suitably about 0.7–1.2 mm, when measured using an optical fiber analyzer such as the Kajaani tester. Cellulose fibers from any source are suitable for use in the invention. Fibers from wood, paper and the like, are particularly suitable.

In accordance with the invention, at least some of the cellulose fibers are combined with a partially neutralized carboxylic acid odor control agent which can be HMCA, PCA, or a HMCA/PCA combination. The degree of neutralization (DON) of the partially neutralized carboxylic acid odor control agent can range from about 15–95% of the carboxyl groups, and is suitably about 30–90% of the carboxyl groups, desirably about 50–80% of the carboxyl groups. The partial neutralization can be accomplished by reacting some of the carboxyl groups with transition metals such as zinc, cadmium, zirconium, chromium, titanium, copper and the like, to form salts. PCA-based odor control agents include odor control agents based on dicarboxylic acids, tricarboxylic acids, higher polycarboxylic acids, etc., having two or more carboxylic acid groups. HMCA-based odor control agents include, for instance, citric acid, malic acid, tartaric acid, and combinations thereof. For purposes of the invention, the partially neutralized carboxylic acid odor control agent may contain 0–100% by weight partially neutralized HMCA, suitably about 25–100% by weight partially neutralized HMCA, desirably about 50–100% by weight partially neutralized HMCA. The partially neutralized carboxylic acid odor control agent may also contain 0–100% by weight partially neutralized PCA, suitably about 0–75% by weight partially neutralized PCA, desirably about 0–50% by weight partially neutralized PCA.

The odor control system can be prepared by initially mixing the carboxylic acid-based odor control agent in water, suitably at a concentration of about 0.5–10% by weight odor control agent, particularly about 2–8% by weight odor control agent. The pH of the resulting solution can be adjusted, if necessary, to a value of about 2–6, suitably about 3–5. The pH adjustment can be accomplished by adding a basic compound, suitably a transition metal hydroxide, into the aqueous mixture. The transition metal hydroxide reacts with, and partially converts the free carboxylic acid groups to a corresponding metal salt.

Alternatively, the carboxylic acid-based odor control agent can be partially neutralized before it is added to the water.

The cellulose fibers can then be added to the aqueous solution of partially neutralized odor control agent, to form a slurry. The slurry can have a fiber consistency of about 5–75% by weight, suitably about 10–50% by weight, desirably about 15–25% by weight. Desirably, the concentrations of partially neutralized carboxylic acid-based odor control agent and cellulose fibers in the slurry are selected so that the weight ratio of dry partially neutralized carboxylic acid odor control agent to dry cellulose fibers is about 5–20%.

Alternatively, the cellulose fibers can initially be combined with water, and the odor control agent can be added during stirring of the resulting slurry. Regardless of the order of addition, the desired concentrations of the ingredients in the ultimate slurry will be the same. In another embodiment, the cellulose fibers and odor control agent can each be combined with separate quantities of water and stirred, and the solutions can then be combined together.

The slurry may then be blended at ambient temperature using any suitable mixer, for instance, a Hobart mixer. The blending times will vary depending on the amounts of partially neutralized carboxylic acid odor control agent and cellulose fibers in the slurry. The mixing should be sufficient to completely saturate the cellulose fibers with the partially neutralized carboxylic acid odor control agent solution. The mixing time may range from about 15 minutes to three hours, and is suitably about 1–2 hours, desirably about 1.5 hours.

To complete the treatment, the entire slurry can then be heated at an elevated temperature, for a time sufficient to completely remove the water. A convection oven or other suitable heating apparatus may be employed. The elevated temperature may be about 50–95° C., suitably about 60–85° C., desirably about 70–80° C. In one embodiment, the heating is performed in stages. For instance, the slurry may be heated at 50° C. for about 6 hours, then at 95° C. for a long enough period of time to completely remove the remaining water, leaving only dry cellulose fibers treated with the odor control agent. The resulting treated cellulose fibers are typically in the form of a sheet or bundle. Depending on the heating temperature, the heating mechanism, the thickness of the sheet or bundle, the amount of water and other factors, the required heating time may vary widely.

The sheet or bundle of treated cellulose fibers is then fiberized, to break apart the fibers. A Pullman fiberizer or other suitable device may be used for this purpose. In one embodiment, the resulting individual treated fibers may be further heated (i.e., cured) in a convection oven at a temperature of about 150–200° C., for a period of 0.5–3 minutes, desirably 1–2 minutes, in order to promote the esterification reaction.

The resulting odor control system will contain a quantity of odor control agent chemically linked and/or otherwise bound to the cellulose fibers. The amount of odor control agent in the system will vary depending on the amount and type of partially neutralized carboxylic acid odor control agent added to the solution (i.e., the amount and type of partially neutralized HMCA and/or PCA), the amount of solution mixed with the cellulose fibers, and the drying temperature and time. The dry odor control system may contain about 1–40% of the carboxylic acid odor control agent, suitably about 3–30% of the carboxylic acid odor control agent, desirably about 5–20% of the carboxylic acid odor control agent based on the combined weight of dry odor control agent and dry cellulose fibers.

In another embodiment of the invention, the acidic odor control agent may be a chelating agent. Suitable chelating agents include without limitation aminopolycarboxylic acids, their alkali metal salts, and combinations thereof. Suitable aminopolycarboxylic acids and alkali metal (preferably sodium) salts thereof, include without limitation ethylenediamine tetraacetic acid (EDTA), the alkali metal salts of EDTA (for instance, $Na_2$ EDTA, $Na_3$ EDTA, and $Na_4$ EDTA), nitrilotriacetic acid, the alkali metal (e.g., sodium) salts of cyclohexanediamine tetraacetic acid, diethylenetriamine pentaacetic acid (DTPA), hydroxyethylenediamine triacetic acid (HEDTA), pentasodium diethylenetriamine pentaacetate, trisodium hydroxyethyl ethylenediamine triacetate, and combinations thereof. A particularly suitable aminopolycarboxylic acid is EDTA. Suitable chelating agents also include polyamino disuccinic acids and alkali metal salts of them, including acids and salts of ethylenediamine-N,N'-disuccinic acid, diethylenetriamine-N,N"-disuccinic acid, triethylenetetraamine-N,N'''-disuccinic acid, 1,6-hexamethylenediamine N,N-disuccinic acid, tetraethylenepentaamine-N,N""-disuccinic acid, 2-hydroxypropylene-1,3-diamine-N,N'-disuccinic acid, 1,2-propylenediamine-N,N'-disuccinic acid, 1,3-propylenediamine-N,N'-disuccinic acid, cis-cyclohexanediamine-N,N'-disuccinic acid, trans-cyclohexanediamine-N,N'-disuccinic acid, and ethylene-bis(oxyethylenenitrilo)-N,N'-disuccinic acid. One suitable polyamino disuccinic acid is ethylenediamine-N,N'-disuccinic acid. Chelating agents can act as odor inhibitors which prevent odor from occurring by interfering with reactions that produce odors, as well as odor absorbents which remove or minimize existing odor-producing compounds.

In another embodiment of the invention, the odor control system may also include a chitin or chitosan odor control agent. The chitin or chitosan can be combined with the partially-neutralized carboxylic acid odor control agent in the aqueous solution, suitably before the solution is combined with the cellulose fibers. In the resulting complex odor control system, the free carboxyl sites on the acidic odor control agent facilitate absorption of ammonia and amine-based odors. The amino groups on the chitin or chitosan facilitate absorption of acid-based odor compounds, and suppress the enzymatic decomposition of urine and menses, thereby inhibiting odor generation.

The partially neutralized carboxylic acid odor control agent to be combined with chitin or chitosan, is suitably a partially neutralized PCA, desirably a partially neutralized HMCA such as citric acid, malic acid or tartaric acid. The combination can be accomplished by initially blending a calculated amount of chitin or chitosan with a calculated amount of the aqueous solution of the partially neutralized multi-carboxylic acid odor control agent at room temperature for 30 minutes. The amount of deacetylation in the chitosan should be determined before adding chitosan to the acid solution. The amount of chitosan added to the acid solution should be selected so that the molar equivalent ratio of free amino groups in the chitosan to free carboxyl groups in the multi-carboxylic acid is about 0.2–0.4. The resulting odor control system is useful in absorbing, neutralizing, and inhibiting formation of ammonia, trimethylamine, isovaleric acid, and similar odoriferous compounds.

The partially neutralized carboxylic acid odor control agent can similarly be combined with a wide variety of other odor control agents, suitably in the aqueous solution before the aqueous solution is combined with the cellulose fibers. The other odor control agents include without limitation metal oxides (e.g., zinc oxide), activated carbon, zeolites, chelating agents and the like. It should be noted that the secondary odor control agents will not necessarily chemically react or otherwise bond with either the cellulose fibers or the partially neutralized carboxylic acid odor control agent. Thus, the primary focus of the present invention involves combining the partially neutralized carboxylic acid odor control agent with the cellulose via a reaction and/or bonding which facilitates durable odor control.

The resulting odor control system (including at least cellulose fibers treated with a partially neutralized carboxylic acid odor control agent) can be used alone or in combination with untreated fibers, and can be used in the absorbent core of a personal care absorbent article or a medical absorbent article. Untreated fibers include untreated cellulose fibers, synthetic fibers, and the like. The treated cellulose fibers can also be combined with superabsorbent materials, and with other ingredients used to make an absorbent core. Personal care absorbent articles include without limitation diapers, training pants, swim wear, absorbent underpants, baby wipes, adult incontinence products, feminine hygiene products, and the like. In absorbent articles, the absorbent core is typically contained between a water-permeable cover sheet (body side liner) and a substantially water impermeable outer cover. Medical absorbent articles include, without limitation, garments, underpads, absorbent drapes, bandages, and medical wipes.

Figure 1:
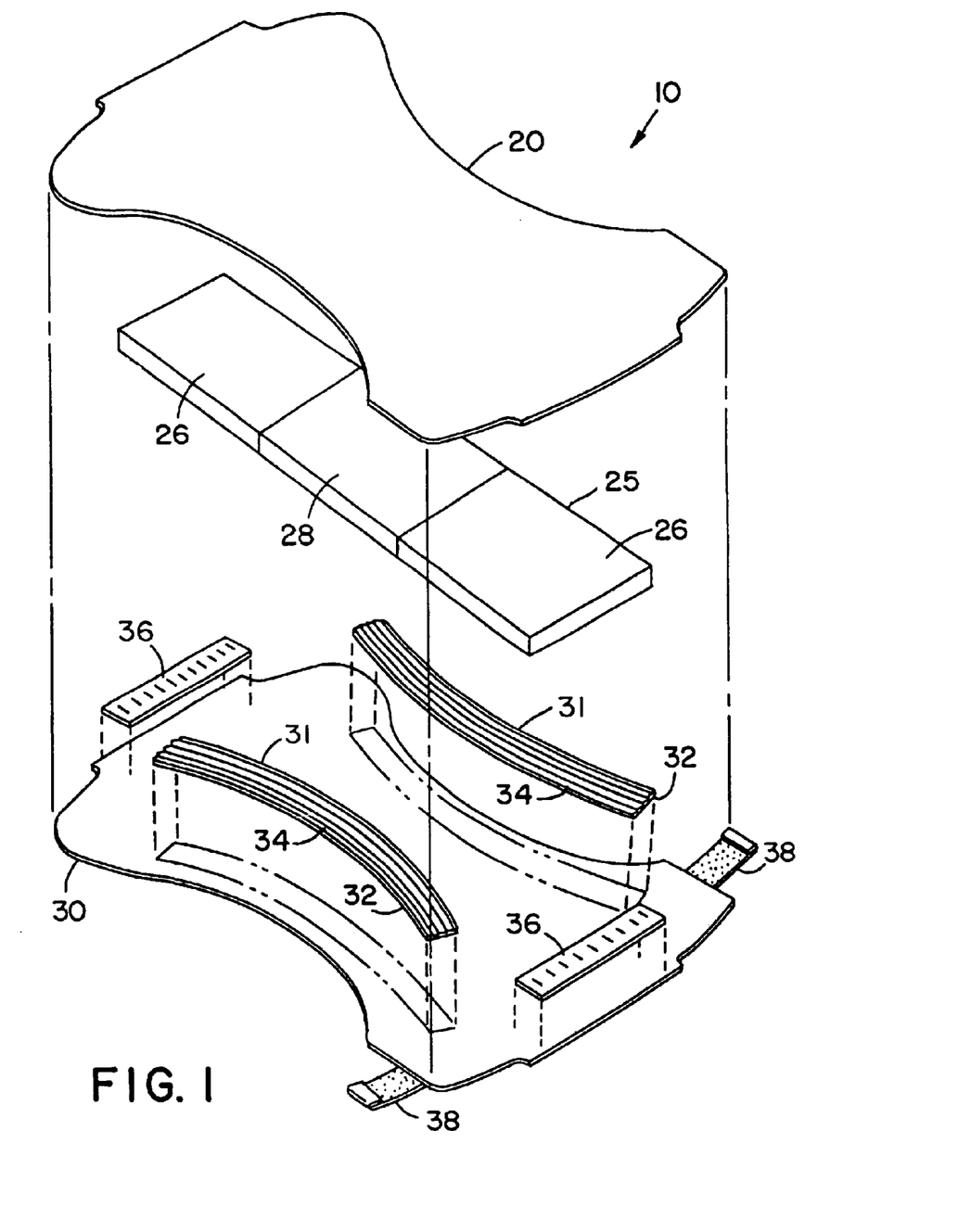
FIG. 1 is an exploded perspective view of a personal care absorbent garment, which is a diaper.

By way of example, FIG. 1 is an exploded perspective view of a disposable diaper according to one embodiment of this invention. Referring to FIG. 1, disposable diaper 10 includes outer cover 30, body-side liner 20, and absorbent core 25 including central region 28 and end regions 26 between body-side liner 20 and outer cover 30. Body-side liner 20 and outer cover 30 are constructed of conventional non-absorbent materials. By "non-absorbent" it is meant that these materials have an absorptive capacity not exceeding 5 grams of 0.9% aqueous sodium chloride solution per gram of material. INDA Standard Test Method IST 10.1 (95), "Standard Test Method for Absorbency Time, Absorbency Capacity, and Wicking Time," published by INDA, Association of the Nonwoven Fabrics Industry, Cary, N.C., provides the basis for a suitable test method to measure absorbency, and is incorporated by reference.

Body-side liner (topsheet) 20 is constructed from highly liquid pervious materials. Body-side liner 20 functions to allow liquid from the wearer to contact the absorbent material or superabsorbent material present in diaper 10. Body-side liner 20 can be made from materials including porous woven materials, porous nonwoven materials, films with apertures, open-celled foams, and batting.

Additionally, a surge layer (not shown) made from nonwoven fibers can be added between body-side liner 20 and absorbent core 25. The surge layer includes surge material having an operable level of density and basis weight to quickly collect and temporarily hold liquid surges, to transport the liquid from its initial entrance point and to substantially release the liquid to absorbent core 25 and the superabsorbent material in absorbent core 25.

One embodiment of diaper 10 includes a barrier tissue between body-side liner 20 and absorbent core 25. Alternatively, the barrier tissue may be between a surge layer and body-side liner 20 or between the surge layer and absorbent core 25. A barrier tissue is beneficial in keeping any loosened superabsorbent material from passing through body-side liner 20 and contacting the user. Barrier tissues are typically natural fiber materials such as any type of wood pulp. Barrier tissues can also be made from uncreped through air-dried (UCTAD) tissue material known in the art.

Outer cover material (backsheet) 30 should be breathable to water vapor. Outer cover 30 desirably includes a material that is substantially liquid impermeable, and can be elastic, stretchable or nonstretchable. The outer cover 30 can be a single layer of liquid impermeable material, but desirably includes a multi-layered laminate structure in which at least one of the layers is liquid impermeable. For instance, the outer cover 30 can include a liquid permeable outer layer and a liquid impermeable inner layer that are suitably joined together thermally, ultrasonically, by a laminate adhesive, or by any other suitable methods known in the art. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture and/or mating fastening component qualities. One example of such a material is a 20 gsm (grams per square meter) spunbond polypropylene nonwoven web. The outer layer may also be made of those materials of which liquid permeable bodyside liner 15 is made. While it is not a necessity for the outer layer to be liquid permeable, it is desired that it provides a relatively cloth-like texture to the wearer.

The inner layer of the outer cover 30 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 30 when a single layer, prevents waste material from wetting articles, such as bedsheets and clothing, as well as the wearer and care giver. A suitable liquid impermeable film for use as a liquid impermeable inner layer, or a single layer liquid impermeable outer cover 30, is a 0.2 millimeter polyethylene film commercially available from Huntsman Packaging of Newport News, Va., U.S.A. If the outer cover 30 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 30. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Generally outer cover 30 will have a moisture vapor transmission rate (MVTR) of at least about 300 grams/$m^2$-24 hours, preferably at least about 1000 grams/$m^2$-24 hours, more preferably at least about 3000 grams/$m^2$-24 hours, measured using INDA Test Method IST-70.4-99, herein incorporated by reference.

Attached to outer cover 30 are waist elastic members 36, fastening tapes 38 and leg elastic members 31. The leg elastics 31 include a carrier sheet 32, which can be a polyolefin film, and individual elastic strands 34. The waist elastic members 36 and the leg elastic members 31 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 31 include a plurality of dry-spun coalesced multifilament spandex elastomeric threads sold under the trade name LYCRA® and available from E.I. DuPont de Nemours and Company, Wilmington, Del., U.S.A.

The diaper of FIG. 1 is a general representation of one basic diaper embodiment. Various modifications can be made to the design and materials of diaper parts. The various layers of article 10 have dimensions which vary depending on the size, shape, and needs of the wearer.

Absorbent core 25 typically includes absorbent materials including natural fibers such as wood pulp fibers. The treated cellulose fibers (odor control system) of the invention may be used in place of untreated natural fibers, or may be combined with untreated natural fibers in any desired ratio. Absorbent core 25 can also include nonwoven fibers or webs. "Nonwoven" and "nonwoven web" refer to materials and webs of material which are formed without the aid of a textile weaving or knitting process. Absorbent core 25 typically includes a matrix of hydrophilic fibers, such as a web of cellulosic fluff, mixed with particles of a superabsorbent material. In a particular embodiment, absorbent core 25 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. Examples of fiber materials used in absorbent core 25 include, without limitation, wood pulp fluff, cotton, wool, silk, polyethylene, polypropylene, polyester, nylon, polyvinyl alcohol, polyacrylonitrile, and polyvinyl chloride.

The superabsorbent material can be in the form of fibers, particles, filaments, or printed or coated onto a fiber matrix. Any conventional superabsorbent material can be used. The superabsorbent material can be substantially homogeneously mixed with the hydrophilic composite fluff matrix or can be nonuniformly mixed. The fluff and superabsorbent particles can also be selectively placed into desired regions of the absorbent core 25 to better contain and absorb body exudates. The concentration of the superabsorbent particles can also vary through the thickness of the absorbent core 25. Alternatively, absorbent core 25 can include a laminate of fibrous webs and superabsorbent material or other suitable means of maintaining a superabsorbent material in a localized area.

EXAMPLE 1
(Control)

100 grams of CR1654 cellulose fibers from the Bowater Co. Coosa mill at Coosa, Ala., was mixed with 1000 ml of water at room temperature for one hour, using a Hobart mixer. Then, the slurry was partially dewatered to a fiber consistency of 30%.

10 grams of anhydrous citric acid from the Aldrich Co. in Milwaukee, Wis. was separately added to 200 ml of water in a beaker. The mixture was stirred until the citric acid crystals were dissolved.

The citric acid solution was added to the cellulose fiber slurry while stirring in the Hobart mixer. The slurry mixture was blended at ambient temperature for 1.5 hours. The slurry mixture was then removed from the Hobart mixer, and heated in a convection oven at 50° C. for 6 hours, then at 95° C. until all of the fibers were dried.

The treated dry cellulose fibers were then fiberized in a Pallman fiberizer, to form individual treated cellulose fibers. The treated cellulose fibers were tested for ammonia absorption and antimicrobiological activity using the procedures described below.

EXAMPLE 2

100 grams of the same cellulose fibers used in Example 1, was mixed with 1000 ml of water at room temperature for one hour, using a Hobart mixer. The slurry was partially dewatered to a fiber consistency of 30%. 10 grams of the same anhydrous citric acid was separately added to 200 ml of water in a beaker. The mixture was stirred until the citric acid dissolved.

7.6 grams of zinc carbonate hydroxide ($5ZnO.2CO_3.4H_2O$, FW=598.87 Reagent Grade, from AESAR Co. in Ward Hill, Mass.) was added slowly with stirring to the citric acid solution. Then, the aqueous citric acid/zinc carbonate hydroxide mixture was added to the cellulose fiber slurry while stirring in the Hobart mixer. The slurry mixture was then blended at ambient temperature for 1.5 hours at a low agitator speed. The slurry mixture was then removed from the Hobart mixer, and heated in a convection oven at 50° C. for 6 hours, then at 95° C. until dry.

The treated dry cellulose fibers were fiberized in a Pallman fiberizer, to form an odor control system of the invention. The odor control system was tested for ammonia absorption and antimicrobiological activity, using the procedures described below.

EXAMPLE 3

100 grams of the same cellulose fibers used in Example 1, was mixed with 1000 ml of water at room temperature for one hour, using a Hobart mixer. The slurry was partially dewatered to a fiber consistency of 30%. 10 grams of the same anhydrous citric acid used in Example 1, and 0.5 grams of polymaleic acid (available from Polysciences, Inc.) were added to 200 ml of water in a beaker. The beaker was stirred until all of the crystals were dissolved. 4.1 grams of zinc oxide (available from Aldrich Co.) was then added slowly with stirring to the water/citric acid/polymaleic acid solution.

The aqueous citric acid/polymaleic acid/zinc oxide mixture was added slowly with stirring to the wet fiber pieces in the Hobart mixer. The resulting mixture was then blended at ambient temperature for 1.5 hours in the Hobart mixer, at a low agitating speed. The resulting mixture was then removed from the Hobart mixer, and heated in a convection oven at 50° C. for 6 hours, then at 95° C. until dry.

The treated dry cellulose fibers were then fiberized in a Pallman fiberizer. The individual treated fibers were cured in a convection oven at 150–200° C. for 1–2 minutes, to form an odor control system of the invention.

Test Methods

Ammonia Absorption

An untreated cellulose sheet and each of the three treated sheets were tested, in duplicate, for ammonia absorption using an analytical method which employed a GC/TCD, which was a gas chromatograph (Hewlett-Packard 5890) equipped with a thermal conductivity detector especially for ammonia measurement. An aliquot of 10 microliters of 30% ammonia hydroxide solution is added to a 20-milliliters glass vial which contains sample. The opening of the glass vial is sealed immediately with a Teflon-lined septum. After one hour of conditioning at room temperature, a gas-tight syringe is used to withdraw one milliliter of headspace, which contains air, water and ammonia gas, from the sealed vial through the septum. The headspace mixture in the syringe is injected into the GC/TCD instrument where ammonia is separated from air and water and detected by a thermal conductivity detector (TCD). By measuring the quantity of ammonia in the headspace of control (untreated fabric) and treated fabric with GC/TCD, the amount of ammonia absorbed by the treated fabric can be determined. Samples of the treated cellulose fiber sheets weighing 0.05 grams each were placed in 20 ml glass vials. To each vial, 10 microliters of a 30% aqueous $NH_4OH$ solution was added, and the vial was immediately sealed. After being conditioned at room temperature for 60 minutes, a gas sample from the headspace in each vial (containing air and ammonia) was withdrawn using a gas tight syringe, and injected into the GC/TCD for ammonia determinations. Each treated cellulose fiber sheet was tested twice, with an untreated cellulose fiber sheet being used as a control.

Bacteriostatic Activity Testing

The bacteriostatic activity testing was performed using Standard Test AATCC-100, of the American Association of Textile Chemists and Colorists. This Test Method is incorporated by reference.

Fiber pH

The fiber pH as measured using TAPPI Standard Method T509 OM-88, which is incorporated by reference.

Test Results

The following Table 1 summarizes the test results for a first control sample of untreated cellulose, a second control sample of citric acid-treated cellulose (with no neutralization of the citric acid), and an odor control system of the invention (Example 2) containing cellulose fibers treated with a partially neutralized citric acid.

TABLE 1

| Code | Citric acid/fiber w/w % | DON % | mgNH3/g fiber | Fiber pH | Bacteriostatic activity |
|---|---|---|---|---|---|
| Control (Untreated CR 1654) | 0 | N/A | 11.5 | 6.8 | None |
| Control (Example 1) | 10 | 0 | 31.8 | 2.3 | None |
| Invention (Example 2) | 10 | 81 | 40.4 | 5 | Very active |

As shown above, only the inventive odor control system (Example 2) helped reduce odor-producing bacteria. The following Table 2 gives the reduction in various odor-producing bacteria after 8 hours of exposure to the inventive odor control system of Example 2.

TABLE 2

| Microorganisms | Log Population Reduction Over Untreated Fiber |
|---|---|
| Citrobacter freundii | 2.13 |
| Escherichia coli | 2.10 |
| Enterobacter aerogenes | 2.79 |
| Staphylococcus aureus | 1.54 |
| Providencia rettgeri | 2.30 |
| Proteus vulgaris | 3.26 |

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent article comprising an odor control system including a non-crosslinked reaction product of cellulose fibers and a partially neutralized carboxylic acid odor control agent reacted in the presence of heat to cause dehydration; the partially neutralized carboxylic acid odor control agent being selected from the group consisting of a partially neutralized HMCA, a partially neutralized PCA, and combinations thereof; the absorbent article being capable of suppressing odor from at least ammonia.

2. The absorbent article of claim 1, wherein the partially neutralized carboxylic acid odor control agent comprises a partially neutralized HMCA selected from the group consisting of partially neutralized citric acid, malic acid, tartaric acid, and combinations thereof.

3. The absorbent article of claim 2, wherein the partially neutralized HMCA comprises partially neutralized citric acid.

4. A diaper comprising the absorbent article of claim 1.

5. Training pants comprising the absorbent article of claim 1.

6. Swim wear comprising the absorbent article of claim 1.

7. Absorbent underpants comprising the absorbent article of claim 1.

8. A baby wipe comprising the absorbent article of claim 1.

9. An adult incontinence product comprising the absorbent article of claim 1.

10. A feminine hygiene product comprising the absorbent article of claim 1.

11. A medical garment comprising the absorbent article of claim 1.

12. An underpad comprising the absorbent article of claim 1.

13. An absorbent drape comprising the absorbent article of claim 1.

14. A bandage comprising the absorbent article of claim 1.

15. A medical wipe comprising the absorbent article of claim 1.

16. The absorbent article of claim 1, wherein the partially neutralized carboxylic acid odor control agent comprises a partially neutralized polycarboxylic acid.

17. The absorbent article of claim 1, wherein the partially neutralized carboxylic acid odor control agent comprises about 25–100% by weight of a partially neutralized hydroxyl multi-carboxylic acid.

18. The absorbent article of claim 1, wherein the partially neutralized carboxylic acid odor control agent comprises about 50–100% by weight of a partially neutralized hydroxyl multi-carboxylic acid.

19. The absorbent article of claim 1, wherein the partially neutralized carboxylic acid odor control agent has a degree of neutralization of about 15–95%.

20. The absorbent article of claim 19, wherein the degree of neutralization is about 30–90%.

21. The absorbent article of claim 19, wherein the degree of neutralization is about 50–80%.

22. The absorbent article of claim 1, wherein the partially neutralized carboxylic acid odor control agent comprises a chelating agent.

23. The absorbent article of claim 1, wherein the partially neutralized carboxylic acid odor control agent comprises a salt of a transition metal.

24. The absorbent article of claim 23, wherein the transition metal is selected from zinc, cadmium, zirconium, chromium, titanium, copper, and combinations thereof.

25. The absorbent article of claim 1, wherein the reaction product comprises about 1–40% of the partially neutralized carboxylic acid odor control agent based on a combined weight of dry odor control agent and dry cellulose fibers.

26. The odor control system of claim 1, wherein the reaction product comprises about 3–30% of the partially neutralized carboxylic acid odor control agent based on a combined weight of dry odor control agent and dry cellulose fibers.

27. The absorbent article of claim 1, wherein the reaction product comprises about 5–20% by weight of the partially neutralized carboxylic acid odor control agent based on a combined weight of dry odor control agent and dry cellulose fibers.

28. The absorbent article of claim 1, further comprising cellulose fibers which are not reacted with the partially neutralized carboxylic acid odor control agent.

29. The absorbent article of claim 1, further comprising a superabsorbent material.

\* \* \* \* \*

UNITED STATES PATENT AND TRADEMARK OFFICE
CERTIFICATE OF CORRECTION

PATENT NO.    : 6,852,904 B2
DATED         : February 8, 2005
INVENTOR(S)   : Tong Sun et al.

It is certified that error appears in the above-identified patent and that said Letters Patent is hereby corrected as shown below:

<u>Title page,</u>
Item [75], Inventors, change the residence of inventor Tong Sun from "Nennah" to -- Neenah --.

Signed and Sealed this

Seventeenth Day of May, 2005

JON W. DUDAS
*Director of the United States Patent and Trademark Office*